(12) United States Patent
Coulthard et al.

(10) Patent No.: US 9,028,459 B2
(45) Date of Patent: *May 12, 2015

(54) REDUCED-PRESSURE DRESSINGS, SYSTEMS, AND METHODS WITH EVAPORATIVE DEVICES

(76) Inventors: Richard Daniel John Coulthard, Verwood (GB); Christopher Brian Locke, Bournemouth (GB)

( * ) Notice: Subject to any disclaimer, the term of this patent is extended or adjusted under 35 U.S.C. 154(b) by 652 days.

This patent is subject to a terminal disclaimer.

(21) Appl. No.: 13/442,076

(22) Filed: Apr. 9, 2012

(65) Prior Publication Data

US 2013/0053795 A1 Feb. 28, 2013

Related U.S. Application Data

(60) Provisional application No. 61/529,722, filed on Aug. 31, 2011, provisional application No. 61/529,709, filed on Aug. 31, 2011, provisional application No. 61/529,735, filed on Aug. 31, 2011, provisional application No. 61/529,751, filed on Aug. 31, 2011.

(51) Int. Cl.
| | | |
|---|---|---|
| *A61M 1/00* | (2006.01) | |
| *A61F 13/02* | (2006.01) | |
| *A61M 27/00* | (2006.01) | |
| *A61M 5/178* | (2006.01) | |
| *A61M 5/00* | (2006.01) | |
| *A61M 5/32* | (2006.01) | |

(Continued)

(52) U.S. Cl.
CPC ..... *A61F 13/00055* (2013.01); *Y10T 29/49826* (2015.01); *A61F 13/0216* (2013.01); *A61M 1/0058* (2013.01); *A61M 27/00* (2013.01); *A61M 1/009* (2014.02)

(58) Field of Classification Search
CPC ......... A61M 1/00; A61M 5/178; A61M 5/00; A61M 5/32; A61M 35/00; A61F 13/00
See application file for complete search history.

(56) References Cited

U.S. PATENT DOCUMENTS

| | | | |
|---|---|---|---|
| 1,355,846 A | 10/1920 | Rannells | |
| 2,052,869 A * | 9/1936 | Coanda | ...................... 239/418 |
| 2,547,758 A | 4/1951 | Keeling | |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Tatyana Zalukaeva
*Assistant Examiner* — Ilya Treyger

(57) ABSTRACT

Wounds dressings, systems, and methods are presented for removing liquid from a wound site into a dressing and moving air through the dressing to evaporate at least a portion of the removed liquid. The air is moved in one instance by a Coanda device incorporated into the dressing. Other systems, dressings, and methods are presented.

16 Claims, 8 Drawing Sheets

(51) Int. Cl.
*A61M 35/00* (2006.01)
*A61F 13/00* (2006.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0032762 A1 | 2/2007 | Vogel |
| 2010/0106079 A1* | 4/2010 | Alimi .............................. 604/24 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| DE | 202010009148 U1 | 9/2010 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 01/85248 A1 | 11/2001 |
| WO | 2005/051461 A1 | 6/2005 |
| WO | 2009/111657 A2 | 9/2009 |
| WO | 2011/130570 A1 | 10/2011 |
| WO | WO 2011/130570 A1 * | 10/2011 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastman, RN; "When Wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N. A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

International Search Report and Written Opinion for corresponding PCT/US2012/032806, mailed Oct. 1, 2012.

* cited by examiner

REDUCED-PRESSURE DRESSINGS, SYSTEMS, AND METHODS WITH EVAPORATIVE DEVICES

RELATED APPLICATIONS

The present invention claims the benefit, under 35 USC §119(e), of the following filings of U.S. Provisional Patent Application Ser. No. 61/529,722, entitled "REDUCED-PRESSURE DRESSINGS, SYSTEMS, AND METHODS WITH EVAPORATIVE DEVICES," filed on 31 Aug. 2011, which is incorporated herein by reference for all purposes; U.S. Provisional Patent Application Ser. No. 61/529,709, entitled "EVAPORATIVE FLUID POUCH AND SYSTEMS FOR USE WITH BODY FLUIDS," filed 31 Aug. 2011, which is incorporated herein by reference for all purposes; U.S. Provisional Patent Application Ser. No. 61/529,735, entitled "ABSORBENT POLYMER DRESSINGS, SYSTEMS, AND METHODS EMPLOYING EVAPORATIVE DEVICES," filed 31 Aug. 2011, which is incorporated herein by reference for all purposes; U.S. Provisional Patent Application Ser. No. 61/529,751, entitled "REDUCED-PRESSURE INTERFACES, SYSTEMS, AND METHODS EMPLOYING A COANDA DEVICE," filed on 31 Aug. 2011, which is incorporated herein by reference for all purposes; and U.S. patent application Ser. No. 13/084,813, entitled "DRESSINGS AND METHODS FOR TREATING A TISSUE SITE ON A PATIENT," filed on 12 Apr. 2011, which is incorporated herein by reference for all purposes.

TECHNICAL FIELD

The present disclosure relates generally to medical treatment systems for treating wounds that produce liquids, such as exudate, and more particularly, but not by way of limitation, to reduced-pressure medical dressings, systems, and methods with evaporative devices.

BACKGROUND

Caring for wounds is important in the healing process. Wounds often produce considerable liquids, e.g., exudate. Medical dressings are often used in wound care to address the production of liquids from the wound. If not properly addressed, liquids at the wound can lead to infection or maceration of the periwound area. As used throughout this document, "or" does not require mutual exclusivity. Wound dressings may be used alone or as an aspect of applying reduced pressure to a tissue site.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue.

SUMMARY

According to an illustrative embodiment, a wound treatment system for treating a wound on a patient includes a treatment manifold for disposing proximate to the wound. The treatment manifold has a first side and a second, patient-facing side. The wound treatment system further includes a first sealing member for disposing over the first side of the treatment manifold to create a sealed space containing the treatment manifold. The first sealing member comprises a high-moisture-vapor-transfer-rate drape. The wound treatment system also includes an air-movement manifold having a first side and a second, patient-facing side. The second, patient-facing side is disposed proximate to the first side of the first sealing member. The wound treatment system further includes a second sealing member disposed over the first side of the air-movement manifold forming a channel space, at least one port formed on the second sealing member for allowing air to exit the channel space, and a reduced-pressure source for producing reduced pressure. The reduced-pressure source is fluidly coupled to the sealed space for delivering reduced pressure thereto. The wound treatment system also includes a pressure source and a Coanda device. The Coanda device is coupled to the second sealing member and fluidly coupled to the pressure source and to the channel space. The Coanda device includes an annular nozzle forming a central opening and having an interior passage and a nozzle opening, and a Coanda surface proximate to and downstream from the nozzle opening, whereby fluid exiting the nozzle opening entrains additional fluid from the central opening and produces a combined fluid flow. The Coanda device is fluidly coupled to a Coanda opening in the second sealing member.

According to another illustrative embodiment, a wound treatment dressing for treating a wound on a patient includes a treatment manifold for disposing on the wound. The treatment manifold has a first side and a second, patient-facing side. The wound treatment dressing also includes a first sealing member for disposing over the first side of the treatment manifold to create a sealed space containing the treatment manifold. The first sealing member comprises a high-moisture-vapor-transfer-rate drape. The wound treatment dressing further includes an air-movement manifold having a first side and a second, patient-facing side. The second, patient-facing side is disposed proximate to the first side of the first sealing member. The wound treatment dressing also includes a second sealing member disposed over the first side of the air-movement manifold to form a channel space, at least one port formed on the second sealing member to allow air to exit the channel space, and a Coanda device coupled to the second sealing member. The Coanda device includes an annular nozzle forming a central opening and having an interior passage and a nozzle opening, and a Coanda surface position proximate to and downstream from the nozzle opening, whereby fluid exiting the nozzle opening entrains additional fluid from the central opening and produces a combined fluid flow. The Coanda device is fluidly coupled to a Coanda opening in the second sealing member.

According to another illustrative embodiment, a wound dressing for treating a wound on a patient includes a means for receiving and retaining liquids from the wound; a means for moving liquid away from the means for receiving and retaining liquids; and a means for evaporating liquid from the means for moving liquid. The means for evaporating a liquid may be a Coanda device.

According to another illustrative embodiment, a method for treating a wound on a patient comprises disposing a treatment manifold proximate to the wound. The treatment manifold has a first side and a second, patient-facing side. The method further includes covering the treatment manifold an a portion of intact skin with a first sealing member to create a sealed space containing the treatment manifold. The first sealing member comprises a high-moisture-vapor-transfer-rate drape and has at least one port. The method also involves disposing an air-movement manifold proximate to the first sealing member, disposing a second sealing member over the air-movement manifold to form a channel space, fluidly coupling a reduced-pressure source to the sealed space for delivering reduced pressure thereto, and coupling a Coanda device to the second sealing member. The method further includes fluidly coupling the Coanda device to a pressure source and to the channel space. The Coanda device includes an annular nozzle forming a central opening and having an interior passage and a nozzle opening, and a Coanda surface proximate to and downstream from the nozzle opening, whereby fluid exiting the nozzle opening entrains additional fluid from the central opening and produces a combined fluid flow. The method further includes fluidly coupling the Coanda device to a Coanda opening in the second sealing member and providing positive pressure to the Coanda device to cause fluid flow within the air-movement manifold.

According to another illustrative embodiment, a wound treatment system for treating a wound on a patient includes a treatment manifold for disposing on the wound. The treatment manifold has a first side and a second, patient-facing side. The wound treatment system further includes a first sealing member for disposing over the first side of the treatment manifold to create a sealed space containing the treatment manifold. The first sealing member comprises a high-moisture-vapor-transfer-rate drape and an air-movement manifold having a first side and a second, patient-facing side. The second, patient-facing side of the air-movement manifold is disposed proximate to the first side of the first sealing member. The wound treatment system includes a second sealing member disposed over the first side of the air-movement manifold to form a channel space and at least one exhaust port formed on the second sealing member for allowing air to exit the channel space. The system further includes a first pump for producing reduced pressure. The first pump is fluidly coupled to the sealed space for delivering reduced pressure thereto. The wound treatment system also includes a second pump for producing a positive pressure. The second pump is fluidly coupled to the channel space; and wherein the first pump and second pump are at least 5 centimeters from the first sealing member.

According to another illustrative embodiment, a wound treatment system for treating a wound on a patient includes a treatment manifold for disposing on the wound, wherein the treatment manifold has a first side and a second, patient-facing side; a first sealing member for disposing over the first side of the treatment manifold and a portion of intact skin to create a sealed space containing the treatment manifold, wherein the first sealing member comprises a high-moisture-vapor-transfer-rate drape; an air-movement manifold having a first side and a second, patient-facing side, wherein the second, patient-facing side is disposed proximate to the first side of the first sealing member; a second sealing member disposed over the first side of the air-movement manifold forming a channel space; and at least one exhaust port formed on the second sealing member for allowing air to exit the channel space. The system further includes a pump for producing reduced pressure, wherein the pump is fluidly coupled to the sealed space for delivering reduced pressure thereto and fluidly coupled to the channel space for delivering reduced pressure thereto.

According to another illustrative embodiment, a wound treatment system for treating a wound on a patient includes a treatment manifold for disposing on the wound, wherein the treatment manifold has a first side and a second, patient-facing side; a first sealing member for disposing over the first side of the treatment manifold and a portion of intact skin to create a sealed space containing the treatment manifold, wherein the first sealing member comprises a high-moisture-vapor-transfer-rate drape; an air-movement manifold having a first side and a second, patient-facing side, wherein the second, patient-facing side is disposed proximate to the first side of the first sealing member; a second sealing member disposed over the first side of the air-movement manifold forming a channel space; and at least one exhaust port formed on the second sealing member for allowing air to exit the channel space. The system further includes a first interface fluidly coupled to the sealed space; a second interface fluidly coupled to the channel space; a first reduced-pressure conduit fluidly coupled to the first interface; a second-reduced pressure conduit fluidly coupled to the second interface; and a pump for producing reduced pressure. The pump is fluidly coupled to the first reduced-pressure conduit and to the second reduced-pressure conduit to deliver reduced pressure to the first reduced-pressure conduit and to the second reduced-pressure conduit.

According to another illustrative embodiment, a wound treatment system for treating a wound on a patient includes a treatment manifold for disposing on the wound, wherein the treatment manifold has a first side and a second, patient-facing side; a first sealing member for disposing over the first side of the treatment manifold and a portion of intact skin to create a sealed space containing the treatment manifold, wherein the first sealing member comprises a high-moisture-vapor-transfer-rate drape; an air-movement manifold having a first side and a second, patient-facing side, wherein the second, patient-facing side is disposed proximate to the first side of the first sealing member; and a second sealing member disposed over the first side of the air-movement manifold forming a channel space. The system further includes at least one exhaust port formed on the second sealing member for allowing air to exit the channel space; a plurality of bellows extending from the second sealing member through at least the first sealing member; a first reduced-pressure source fluidly coupled to the sealed space; and a second reduced-pressure source fluidly coupled to the plurality bellows and operable to cause the bellows to move from a first, free state to a second, collapsed state under reduced pressure, whereby at least some air in the air-movement manifold is forced out the at least one exhaust port.

Other aspects, features, and advantages of the illustrative embodiments will become apparent with reference to the drawings and detailed description that follow.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments are defined only by the appended claims.

Figure 1:
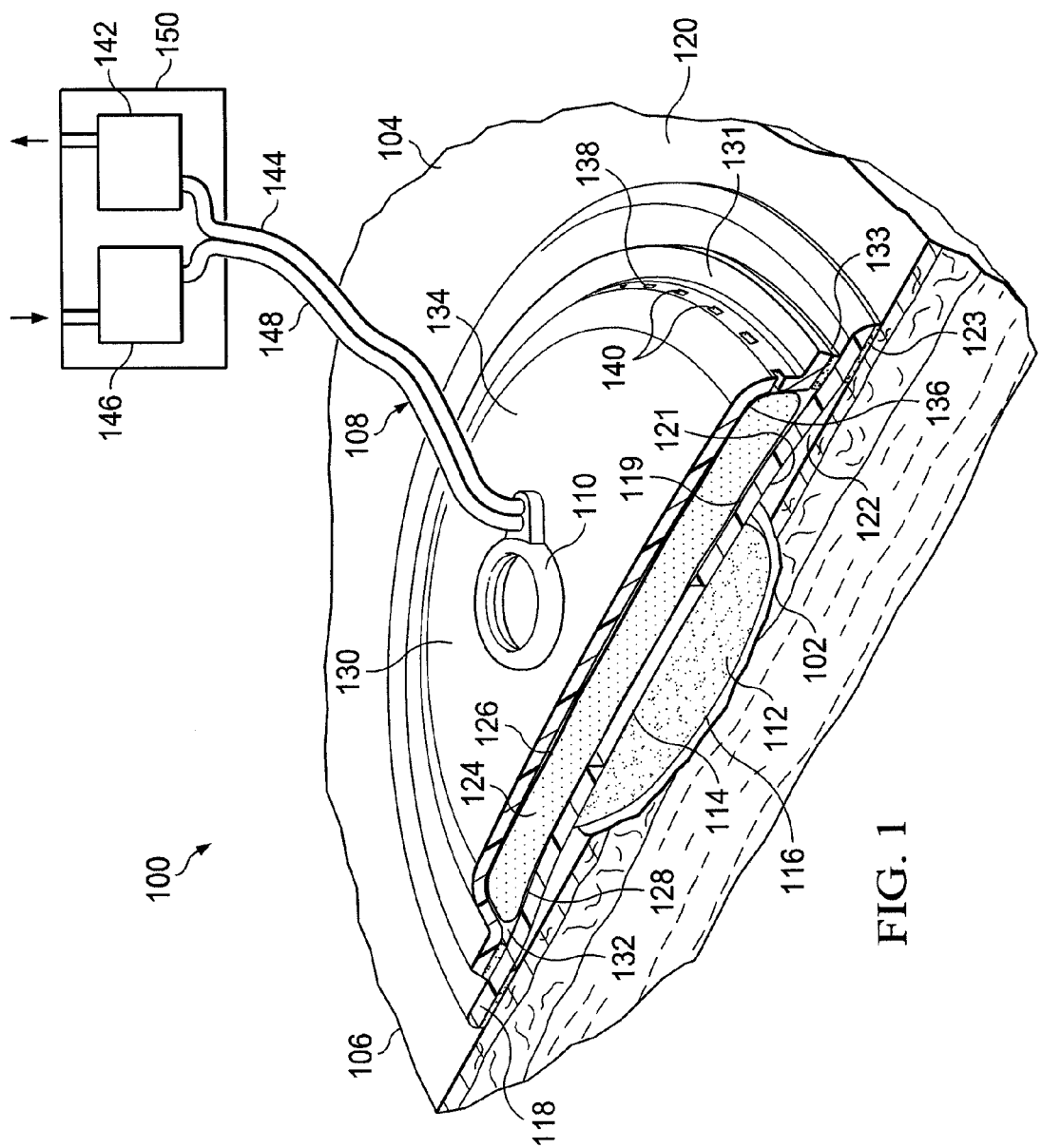
FIG. 1 is a schematic, perspective view, with a portion shown in cross section, of an illustrative embodiment of a wound treatment system for treating a wound on a patient.

Referring now to the drawings and initially to FIG. 1, an illustrative embodiment of a wound treatment system 100 for treating a wound 102 on a patient 104 is presented. The wound 102 may any damaged or irregular tissue. The wound 102 is shown extending partially through epidermis 106. The wound treatment system 100 is particularly well suited for wounds that produce liquids. An evaporative subsystem 108 helps remove fluids from the system 100. In this embodiment, the evaporative subsystem 108 includes a Coanda device 110 as will be described further below.

The wound treatment system 100 includes a treatment manifold 112 for disposing proximate to the wound. The treatment manifold 112 has a first side 114 and a second, patient-facing side 116. The treatment manifold 112 is for distributing reduced pressure to and receiving fluids, including liquids, from the wound 102, and may be any material that functionally carries out these tasks. Manifold generally refers to a substance or structure that is provided to assist in applying reduced pressure to, delivering fluids to, or removing fluids from a tissue site or wound. Examples of treatment manifolds 112 may include, without limitation, one or more of the following: devices that have structural elements arranged to form flow channels, such as, for example, cellular foam, open-cell foam, porous tissue collections, liquids, gels, and foams that include, or cure to include, flow channels; porous material porous, such as foam, gauze, felted mat, or any other material suited to a particular biological application; or porous foam that includes a plurality of interconnected cells or pores that act as flow channels, e.g., a polyurethane, open-cell, reticulated foam such as GranuFoam® material manufactured by Kinetic Concepts, Incorporated of San Antonio, Tex.; a bioresorbable material; or a scaffold material.

The treatment manifold 112 is covered by a first sealing member 118. The first sealing member 118 is disposed over the first side 114 of the treatment manifold 112 and a portion of intact skin 120 to create a sealed space 122 containing the treatment manifold 112. The first sealing member 118 may be adhered to the intact skin 120 by an attachment device 123, e.g., an adhesive, and to the first side 114 of the treatment manifold 112. The first sealing member 118 comprises a high-moisture-vapor-transfer-rate drape. "Moisture Vapor Transmission Rate" or "MVTR" represents the amount of moisture that can pass through a material in a given period of time. A first high-moisture-vapor-transfer-rate drape typically has a moisture vapor transmission rate greater than 300 $g/m^2/24$ hours and more typically 1000 $g/m^2/24$ hours or more. The first sealing member 118 allows vapor to egress from the treatment manifold 112 through first sealing member 118 and into an air-movement manifold 124. The first sealing member 118 has a first side 119 and a second, patient-facing side 121.

The first sealing member 118 may comprise any of numerous materials, such as any of the following: hydrophilic polyurethanes, cellulosics, hydrophilic polyamides, polyvinyl alcohol, polyvinyl pyrrolidone, hydrophilic silicone polymers, hydrophilic acrylics, hydrophilic silicone elastomers and copolymers of these. As one specific, illustrative, non-limiting embodiment, the first sealing member 118 may be formed from a breathable cast mat polyurethane film sold under the name INSPIRE 2301 from Expopack Advanced Coatings of Wrexham, United Kingdom. That illustrative sealing member has a MVTR (inverted cup technique) of 14500-14600 $g/m^2/24$ hours. See www.exopackadvancedcoatings.com. The first sealing member 118 may have various thicknesses, such as 10 to 40 microns (μm), e.g. 15, 20, 25, 30, 35, 40 microns or any number in the stated range.

As previously noted, the first sealing member 118 may be adhered to the intact skin 120 by an attachment device 123, e.g., an adhesive, and to the first side 114 of the treatment manifold 112. The performance of the first sealing member 118 with respect to MVTR may be enhanced by only covering a limited surface area of the second, patient-facing side 121 of the first sealing member 112 with the attachment device 123. For example, only the peripheral edge of the first sealing member 118 may be covered or a limited pattern may be used. In the latter situation, according to one illustrative embodiment, only 30 to 60 percent of the surface area is covered with the attachment device 123. The limited coverage by the attachment device 123 on the second, patient-facing side 121 may be accomplished by applying the attachment device 123 in a pattern, e.g., grid, spaced dots, swirls, or other patterns. In another embodiment, the first sealing member 118 may be coupled by welding (e.g., ultrasonic or RF welding), bonding, stitching, staples, or another coupling device to the first side 114 of the treatment manifold 112. The attachment device 123 may be applied only to a peripheral portion of the first sealing member 118.

The air-movement manifold 124 has a first side 126 and a second, patient-facing side 128. The second, patient-facing side 128 is disposed proximate to the first side 119 of the first sealing member 118. The air-movement manifold 124 provides open pathways for airflow even when under compression developed by the system 100. The air-movement manifold 124 may be any substance that carries out these functions. The air-movement manifold 124 may be, for example, one or more of the following: open cell foam, woven or non-woven material, porous polymer, molded matrix, or sintered polymers.

A second sealing member 130 disposed over or covers the first side of the air-movement manifold 124 forming a channel space 132. The second sealing member 130 has a first side 134 and a second, patient-facing side 136. The second, patient-facing side 136 of the second sealing member 130 is disposed against the first side 126 of the air-movement manifold 124. The second sealing member 130 may have an extension portion 131 that is attached by an attachment device 133 to a portion of the first sealing member 118 or otherwise sealed. The second sealing member 130 may be formed from one or more of the following materials: all those mentioned for the first sealing member 118, as well as low MVTR films. Woven and non-woven materials may also be used as long as the materials are constructed or coated such that the materials adequately contain and control the air flow.

The second sealing member 130 helps direct airflow in the channel space 132 and may allow egress of vapors. At least one port 138 is formed on the second sealing member 130 for allowing air to exit the channel space 132. More typically, a plurality of ports 140 are formed through the second sealing member 130 and are typically spaced from the Coanda device 110 or other air mover. A bacterial filter (not shown) may cover each of the plurality of ports 140 as a safeguard against bacteria entering the wound 102 if a breach is created in the first sealing member 118. As with the first sealing member 118, the second sealing member 130 may have limited coverage on the second, patient-facing side 136 of the attachment device 133.

The wound treatment system 100 includes a reduced-pressure source 142 for producing reduced pressure. The reduced-pressure source 142 is fluidly coupled to the sealed space 122 for delivering reduced pressure to the sealed space 122. The reduced pressure is used to treat the tissue at the wound 102 and to remove fluids, including liquids, from the wound 102. The reduced-pressure source 142 may be a vacuum pump, wall suction, micro-pump, or other source.

The reduced-pressure source 142 is fluidly coupled to the sealed space 122 by a reduced-pressure conduit 144. The reduced-pressure conduit 144 is shown associated with the Coanda device 110. Yet it should be understood that the reduced-pressure conduit 144 may separately extend through the second sealing member 130, air-movement manifold 124, first sealing member 118 and into the treatment manifold 112 or may be fluidly coupled using a reduced-pressure interface (e.g., a Sensi-TRAC interface available from KCI, Inc. of San Antonio, Tex.); or any other means.

The wound treatment system 100 further includes a pressure source 146, which is a positive-pressure source, that is fluidly coupled to the Coanda device 110. The pressure source 146 may be any source of positive pressure including, without limitation, a pump, a wall source, a pressurize canister, or other means. A diaphragm pump is well suited in many applications. The pressure source 146 is fluidly coupled to the Coanda device 110 by a conduit 148. The pressure source 146 may be housed with the reduced-pressure source 142 in a pressure unit 150.

The Coanda device 110 is a device for entraining air for desired purpose using the Coanda effect. The Coanda effect is generally phenomena in which a flow attaches itself to a nearby surface and remains attached even as the surface (Coanda surface) pulls away from the flows initial direction. As the flow curves away, it will entrain surrounding fluids and increasing the volume of the flow. Without being limited to theory, it appears that the surface that is brought close to the flow restricts the entrainment in that region and as the flow accelerates to try to balance the momentum transfer, a pressure differential develops across the flow and the direction is changed or deflected closer to the surface. The effect is named for Henri Coanda and the concept is described in U.S. Pat. No. 2,052,869, granted to Coanda.

Thus, in the illustrative embodiment of FIG. 1, the Coanda device 110 creates a desired airflow. The Coanda device 110 is coupled to the second sealing member 130 and fluidly coupled to the pressure source 146 and to the channel space 132. The Coanda device 110 receives positive pressure air from the conduit 148 and develops an enhanced flow that is delivered from the Coanda device 110 into the air-movement manifold 124 and more generally into the channel space 132. The airflow flows through the channel space 132 and air-movement manifold 124 and exits the one or more ports 138, 140.

As the air moves through the channel space 132 and air-movement manifold 124, any moisture or vapor on the first side 119 of the first sealing member 118. This in turn will increase or maintain a humidity gradient across the first sealing member 118 that helps remove liquid from the treatment manifold 112. That in turn provides many benefits including an increased ability to process liquids. It should be noted that other entrainment devices may be used as the Coanda device 110 or to entrain air into the dressing to achieve the desired air-flow. These other devices may be used to entrain air to create a more voluminous flow due to the presence of a high pressure flow, such as a Conventional Ejector, where a primary flow is located proximate to an available secondary air source that is "dragged" by an aerofoil shape to have the effect of an air-multiplier.

Figure 2:
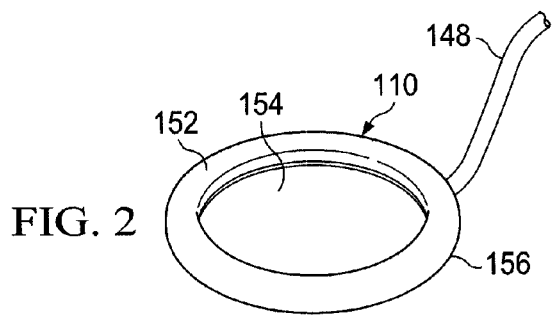
FIG. 2 is a schematic, perspective view of an illustrative embodiment of a Coanda device.
Figure 3:
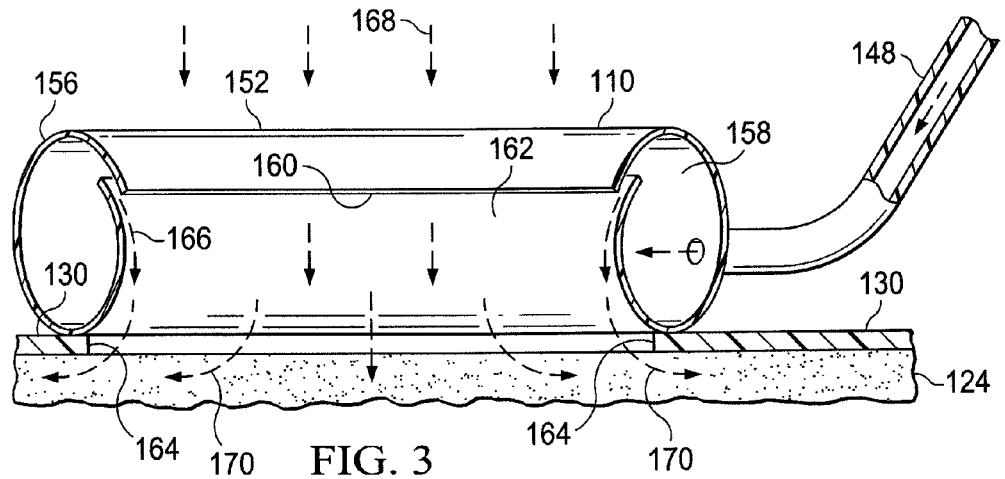
FIG. 3 is a schematic cross section of the Coanda device of FIG. 2.

Referring now primarily to FIGS. 2-3, an illustrative Coanda device 110 is presented. The Coanda device 110 includes an annular nozzle 152. The annular nozzle 152 forms a central opening 154. The annular nozzle 152 has walls 156 that form an interior passage 158. A nozzle opening 160 is formed on the annular nozzle 152 towards the central opening 154. A portion of the walls 156 forms a Coanda surface 162 proximate to and downstream from the nozzle opening 160. The fluid or air exiting the nozzle opening 160 entrains additional fluid from the central opening 154 as the flow follows the Coanda surface 162. The flow of air plus the entrained air produce a combined fluid flow. The Coanda device 110 is fluidly coupled to a Coanda opening 164 or aperture in the second sealing member 130 that allows the flow into the channel space 132 and air-movement manifold 124.

For the configuration shown, air is moved out of the nozzle opening 160 as suggested by arrows 166 in FIG. 3. The airflow entrains additional air from the central opening 154 as suggested by arrows 168. The combined fluid flow is suggested by arrows 170. It should be apparent that if a volume $V_1$ of air is delivered by conduit 148 to the Coanda device 110 over a time T and a volume $V_2$ of air is delivered through the central opening 154 of the Coanda device over time T, the combined air flow $(V_2+V_1)$ will be enhanced. It should be understood that the Coanda device 110 may be flipped as well such that the nozzle opening 160 discharges air away from the second sealing member 130 and air that is recruited from the central opening 154 is pulled from the Coanda opening 164 in the second sealing member 130. In this latter embodiment, the Coanda device 110 is configured to pull fluid from the Coanda opening 164 thereby pulling fluid from the at least one port 138 through the air-movement manifold 124 and out the Coanda opening 164. A high pressure flow is delivered to the Coanda device 110 and a low pressure flow is created with the combined fluid flow.

Figure 4:
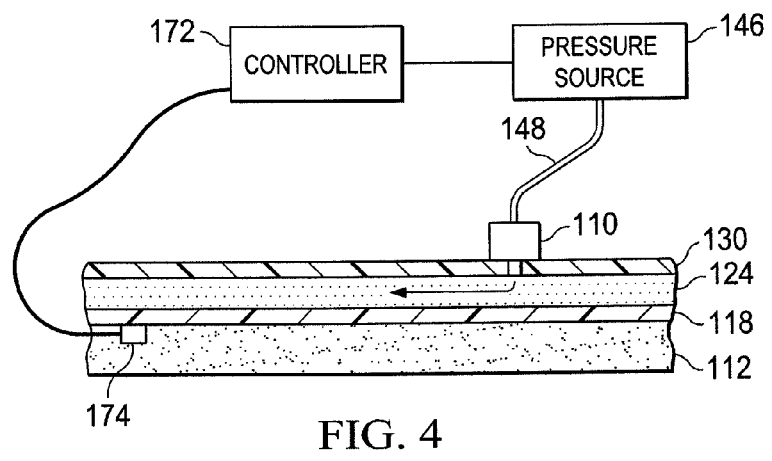
FIG. 4 is a schematic diagram of a wound treatment system for treating a wound on a patient.

Referring now to FIG. 4, a diagram of the wound treatment system 100 is presented that demonstrates active control of the system 100. The wound treatment system 100 of FIG. 4 is analogous to FIG. 1, except a controller 172 and a saturation sensor 174 have been added. The saturation sensor 174 is operatively coupled to the treatment manifold 112 and to the controller 172. The controller includes a battery (not explicitly shown). The controller 172 and saturation sensor 174 determine when the treatment manifold 112 is saturated.

Saturated means that the amount of liquid in the treatment manifold 112 has exceeded a first threshold or design threshold. The controller may then activate the pressure source 146 causing airflow in the air-movement manifold 124 to help remove liquids. Likewise, when the controller 172 and saturation sensor 174 determine that the treatment manifold 112 is no longer saturated, the controller 172 may deactivate the pressure source 146.

The saturation sensor 174 may be any device that allows monitoring of the saturation status of the treatment manifold 112. For example, without limitation, the saturation sensor 174 may be a resistive element that changes resistance when liquid covers the resistive elements, a galvanic cell that creates a voltage when covered with liquid from a wound, or a capacitive sensor that changes properties when saturated liquid is nearby, or any other electrical saturation sensor.

Referring generally to FIGS. 1-4, according to one illustrative embodiment, the treatment manifold 112 is disposed proximate to the wound 102. The treatment manifold 112 and a portion of intact skin 120 are covered with the first sealing member 118 to create the sealed space 122 containing the treatment manifold 112. The air-movement manifold 124 is disposed proximate to the first sealing member 118. The second sealing member 130 is disposed over the air-movement manifold 124 to form the channel space 132. The reduced-pressure source 142 is fluidly coupled to the sealed space 122 for delivering reduced pressure thereto.

The Coanda device 110 is coupled to the second sealing member 130. The Coanda device 110 is fluidly coupled to the pressure source 146 and to the channel space 132. The Coanda device 110 is fluidly coupled to the Coanda opening 164 in the second sealing member 130. Positive pressure is then provided from the pressure source 146 to the Coanda device 110 to cause fluid flow within the air-movement manifold 124. The positive pressure may be continuously or intermittently provided to the Coanda device 110. The intermittent cycle may be fixed or variable based on a number of factors such as anticipated saturation, actual saturation, stage of therapy, remaining battery capacity, or other factors. The positive pressure may also be actively controlled using a controller 172 and saturation sensor 174 as discussed in connection with FIG. 4.

The evaporative subsystem 108 includes the air-movement manifold 124, second sealing member 130, and a source of air movement in the air-movement manifold 124, e.g., the Coanda device 110. Other sources of air movement may be used as part of the evaporative subsystem 108.

Figure 5:
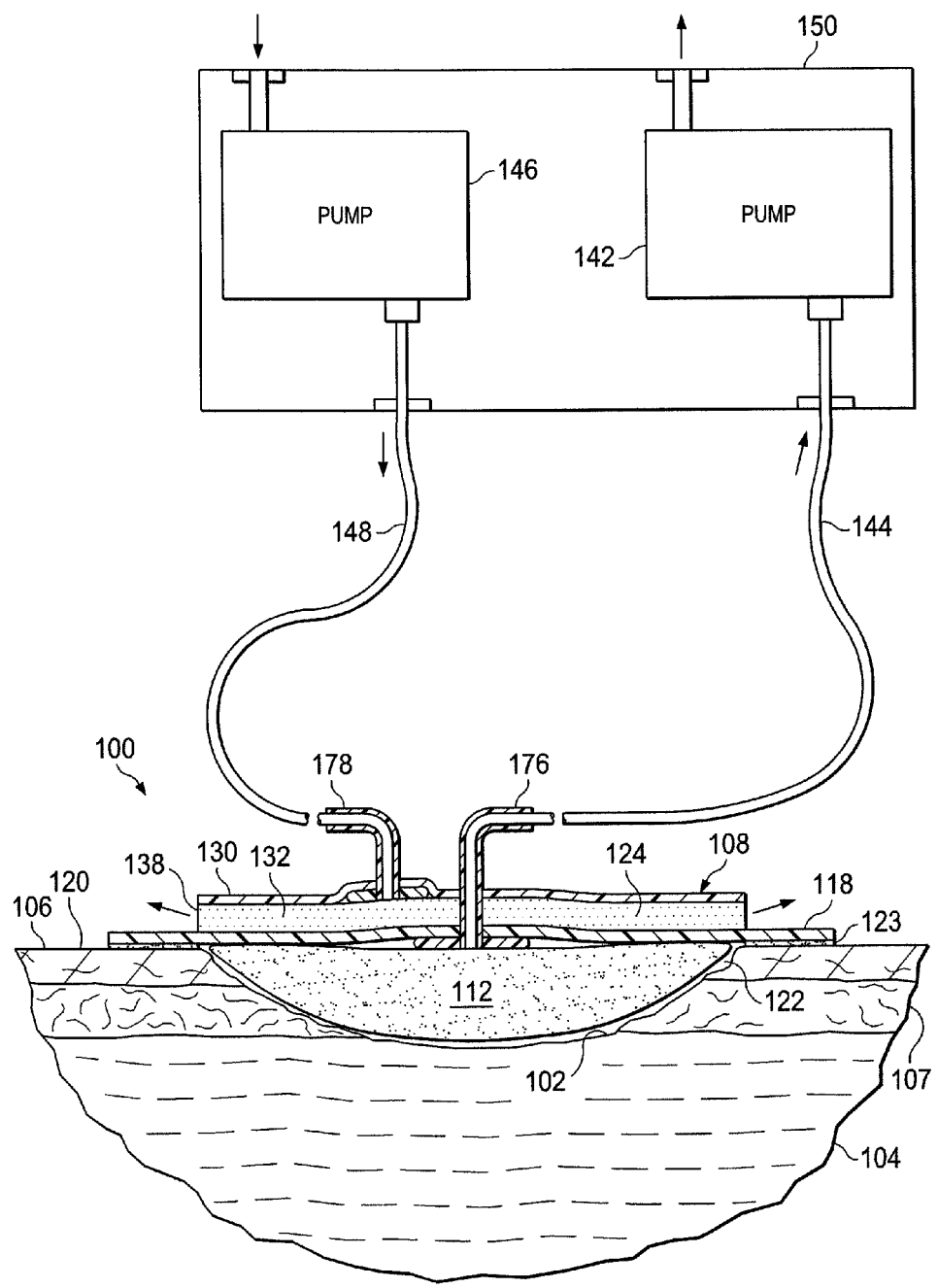
FIG. 5 is a schematic diagram, with a portion shown in cross section, of an illustrative embodiment of a wound treatment system for treating a wound on a patient.

Referring now to FIG. 5, another wound treatment system 100 for treating a wound 102 on a patient 104 is presented. The wound treatment system 100 is analogous in many respects to the wound treatment system 100 of FIG. 1, and accordingly, some parts are labeled but not further discussed. The wound 102 extends through epidermis 106 and dermis 107. In this embodiment, the Coanda device 110 is replaced by delivering positive pressure directly to the channel space 132 and air-movement manifold 124.

The reduced-pressure source 142 may be, for example, a first pump or vacuum pump or any other source as previously mentioned for producing reduced pressure. As before, the reduced-pressure source 142 is fluidly coupled to the sealed space 122 for delivering reduced pressure thereto. A reduced-pressure conduit 144 fluidly couples the reduced-pressure source 142 to a first pressure interface 176. The first pressure interface 176 is fluidly coupled to the sealed space 122.

The pressure source 146 may be a second pump or any other source as previously mentioned. The pressure source 146 is fluidly coupled by a conduit 148 to a second pressure interface 178. The second pressure interface 178 is fluidly coupled to the channel space 132. It should be appreciated that the pressure source 146 may supply positive pressure or may pull air from the second pressure interface 178. In either case, air flow will be produced in the channel space 132.

As with all the embodiments herein, the active control components of FIG. 4 may be readily added to this embodiment as well. The pressure source 146 and reduced-pressure source 142 are remote, e.g., at least 5 centimeters and typically more than 14 centimeters from the first pressure interface 176 and second pressure interface 178 respectively.

Figure 6:
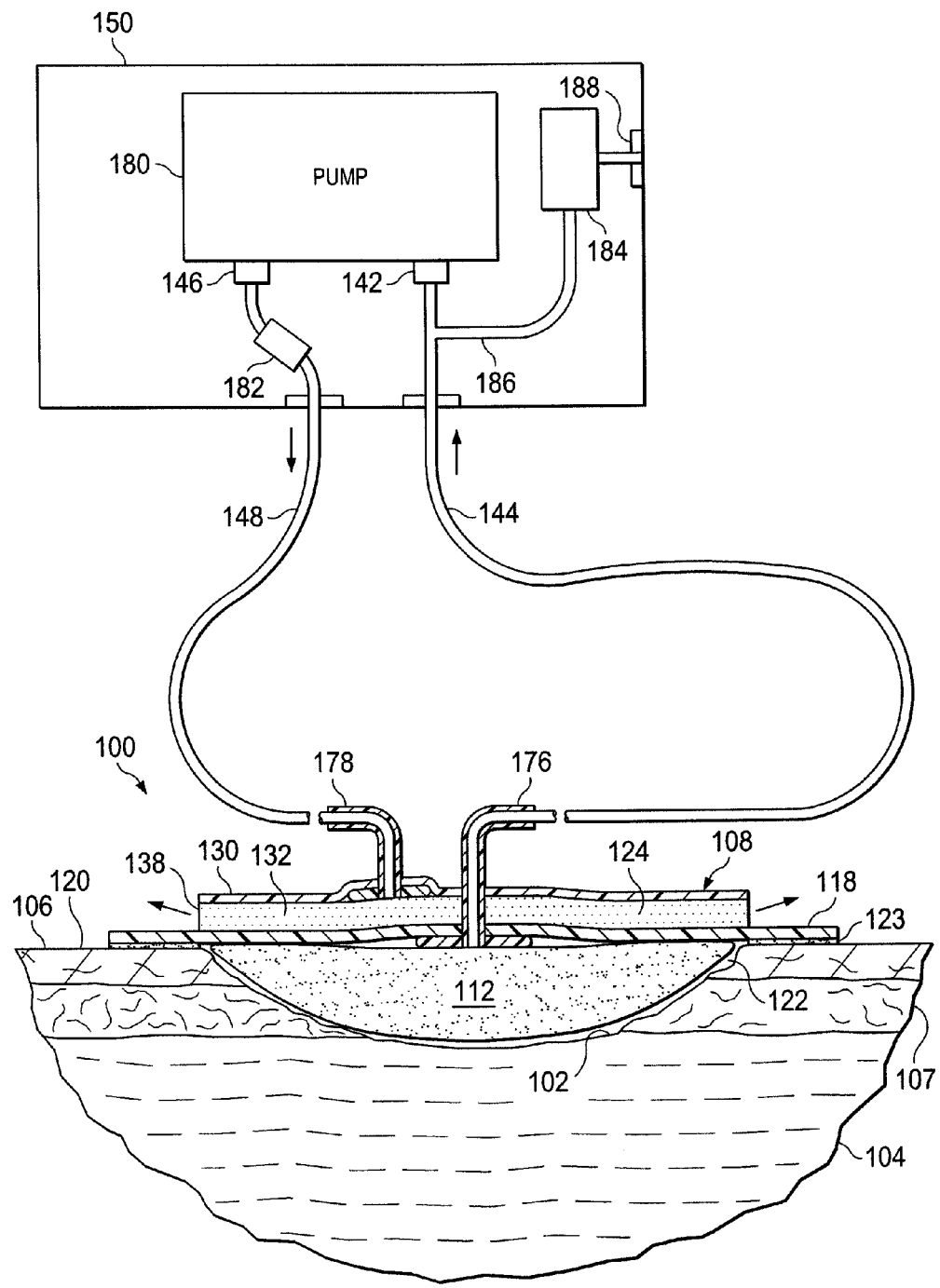
FIG. 6 is a schematic diagram, with a portion shown in cross section, of an illustrative embodiment of a wound treatment system for treating a wound on a patient.

Referring now primarily to FIG. 6, another wound treatment system 100 for treating a wound 102 on a patient 104 is presented. The wound treatment system 100 is analogous in many respects to the wound treatment system 100 of FIGS. 1 and 5, and accordingly, some parts are labeled in FIG. 6 but are not further discussed. In the illustrative embodiment of FIG. 6, a pump 180 is used for the reduced-pressure source 142 and as the pressure source 146. The first pressure interface 176 is fluidly coupled to the sealed space 122, and the second interface 178 is fluidly coupled to the channel space 132. The first conduit 144 is fluidly coupled to the first pressure interface 176. The second conduit 148 is fluidly coupled to the second interface 178. The pump 180 is operable to produce reduced pressure and a positive-pressure exhaust. The pump 180 is fluidly coupled to the first conduit 144 and to the second conduit 148. A bacteria filter 182 is associated with the second conduit 148 for removing bacteria from the air flow therein. The air is thus filtered before entering the channel space 132.

A valve 184 may be on a tributary conduit 186 that is fluidly coupled to the low pressure side of the pump 180. The valve 184 allows air to enter the pump 180 from an inlet 188 once the set reduced pressure is realized in the valve 184. This flow allows the pump 180 to produce exhaust that is delivered to conduit 148. The valve 184 may be a proportional valve or any other type of valve, and typically is selected or adjusted to allow flow to enter the pump 180 when the pressure realized in the conduit 144 is −125 mm Hg or more negative (e.g., −125 to −200 mm Hg).

Figure 7:
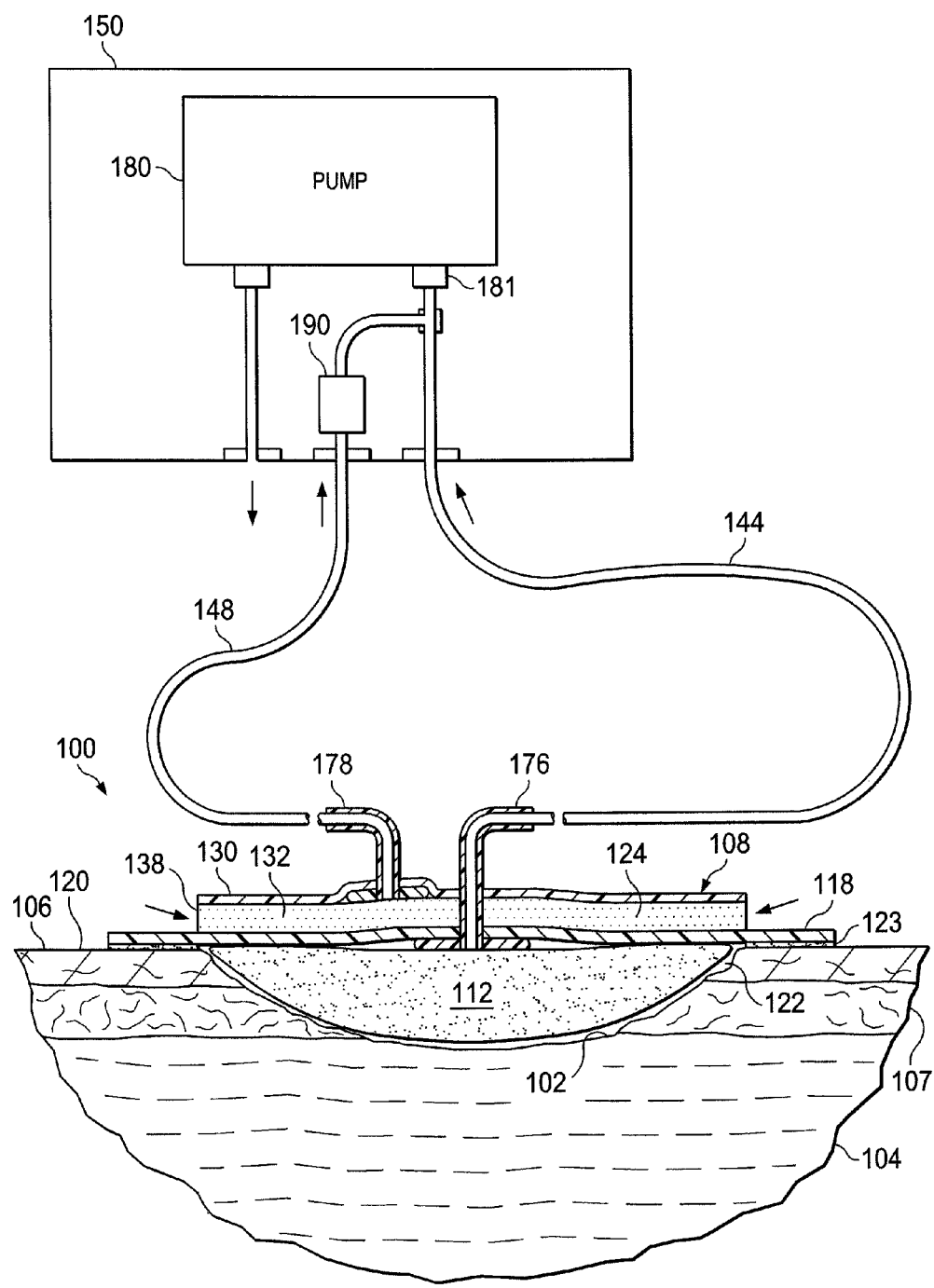
FIG. 7 is a schematic diagam, with a portion shown in cross section, of an illustrative embodiment of a wound treatment system for treating a wound on a patient.

Referring now to FIG. 7, another wound treatment system 100 for treating a wound 102 on a patient 104 is presented. The wound treatment system 100 is analogous in many respects to the wound treatment system 100 of FIGS. 1 and 5, and accordingly, some parts are labeled in FIG. 7 but are not further discussed. In the illustrative embodiment of FIG. 7, a single pump 180 is again used, but this time the low pressure side of the pump 180 is used for the evaporative subsystem 108 and the reduced-pressure treatment at the wound 102.

The low pressure side (suction side) 181 of the pump 180 is fluidly coupled to both the first conduit 144 and second conduit 148. Thus, in this embodiment, air is pulled into the at least one port 138 or plurality of ports, through the air-movement manifold 124, and through second conduit 148 to the pump 180. The pump 180 is sized to have sufficient capacity to simultaneously maintain the desired reduced pressure at the wound 102 and provide sufficient flow through the evaporative subsystem 108. A valve 190 is in line with the second conduit 148 and remains closed until the pressure in the first conduit 144 reaches a threshold reduced pressure. When the threshold reduced pressure is reached, the valve opens and allows flow in the second conduit 148. The valve may be a proportional valve, needle valve, gate valve, or other valve type.

Figure 8:
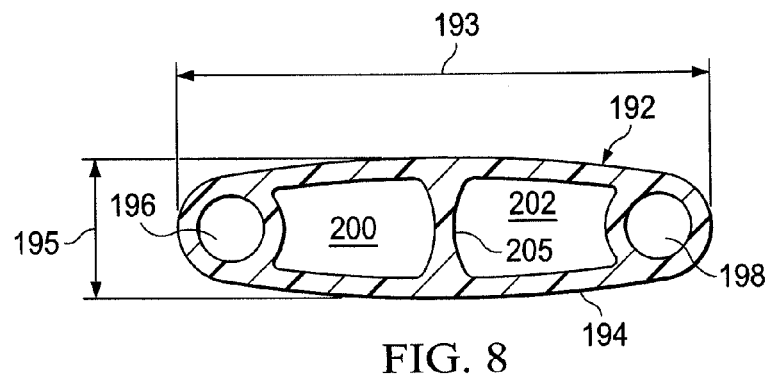
FIG. 8 is a schematic cross section of an illustrative embodiment of a pressure conduit.

Referring now primarily to FIG. 8, a pressure conduit 192 for use with a wound treatment system is presented. The pressure conduit 192 includes a conduit body 194 having an aspect ratio in lateral cross section greater than two. Aspect ratio is the longer dimension 193 over the shorter dimension 195. The pressure conduit 192 has two peripheral conduits 196, 198 and two void passages 200, 202 separated by a support wall 205.

Figure 9:
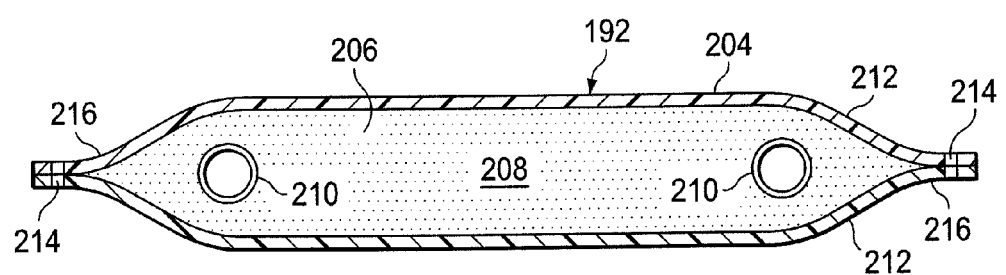
FIG. 9 is a schematic cross section of an illustrative embodiment of a pressure conduit.

Referring now primarily to FIG. 9, another illustrative embodiment of a pressure conduit 192 for use with a wound treatment system, such as wound treatment system 100 in FIG. 1, is presented. The pressure conduit 192 includes a pouch 204 having an interior space 206, a gas-transport material 208 disposed within the interior space 206, and at least one internal conduit 210 disposed within the interior space 206. The pouch 204 may, be formed by two polymer sheets 212 fastened at their lateral edges 216 by a binding 214.

The illustrative conduits of FIGS. 8 and 9 present two alternative ways of carrying two fluid streams for use with the systems herein. These conduits presents alternatives to using dual lumen tubing. The different cross-sections are used to suit the different flow characteristics. In what is now traditional negative pressure wound therapy (NPWT), it is normal for the flow to be relatively low. With the evaporative subsystems 108 used herein, the flow would be higher and a larger cross-section for the conduits would reduce the pressure drop otherwise associated with a small diameter lumen.

Figure 10A:
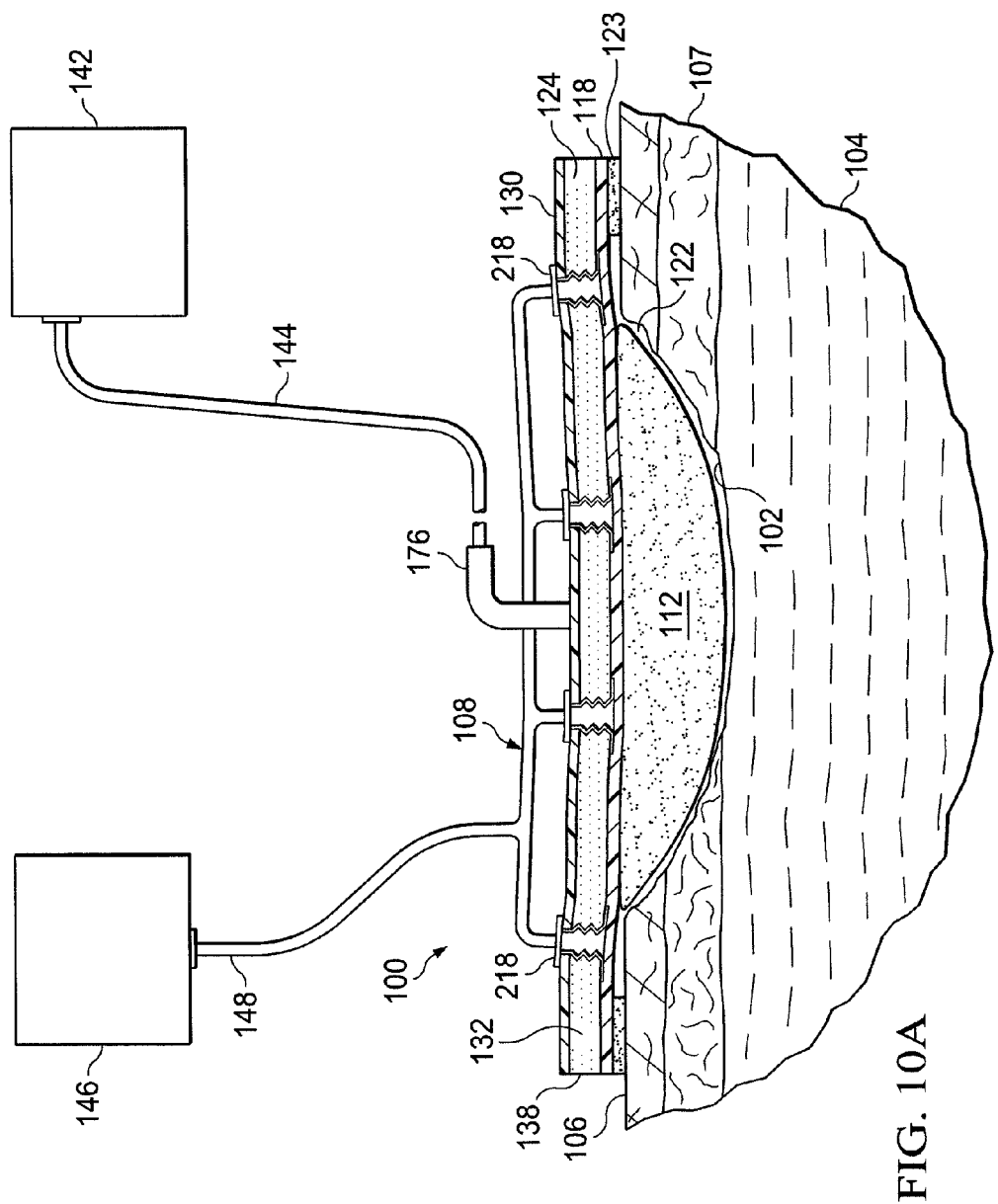
FIG. 10A is a schematic diagram, with a portion shown in cross section, of an illustrative embodiment of a wound treatment system for treating a wound on a patient shown in an extended position.
Figure 10B:
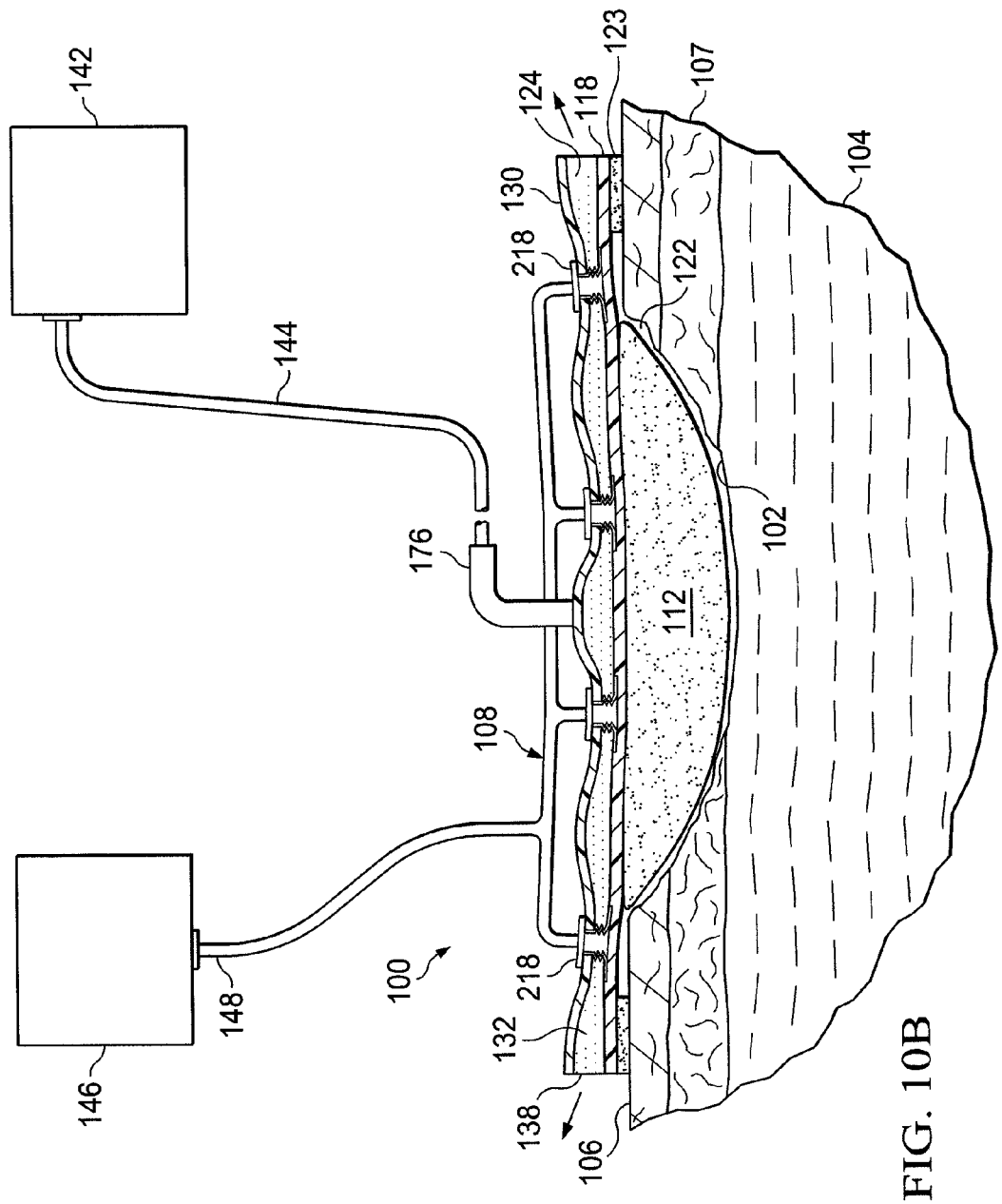
FIG. 10B is a schematic diagram, with a portion shown in cross section, of the illustrative embodiment of a wound treatment system of FIG. 10A shown in a collapse state.

Referring now primarily to FIGS. 10A and 10B, another wound treatment system 100 for treating a wound 102 on a patient 104 is presented. The wound treatment system 100 is analogous in many respects to the wound treatment system 100 of FIGS. 1 and 5, and accordingly, some parts are labeled in FIGS. 10A and 10B, but are not further discussed. As with other embodiments, the wound treatment system 100 includes a treatment manifold 112, a first sealing member 118, a sealed space 122, an air-movement manifold 124, a second sealing member 130, and a channel space 132. In this illustrative embodiment, the evaporative subsystem 108 includes a plurality of bellows 218 extending from the second sealing member 130 through at least the air-movement manifold and may go through the first sealing member 118. A first reduced-press source 142 is fluidly coupled to the sealed space 122.

A pressure source 146, which in this embodiment is a second reduced-pressure source, is fluidly coupled to the plurality of bellows 218. The pressure source 146 is operable to cause the plurality of bellows 218 to move from a first, free state shown in FIG. 10A to a second, collapsed state shown in FIG. 10B under reduced pressure. The collapsed state includes partial collapses. In moving the plurality of bellows 218 from the first state to the second state at least some air in the air-movement manifold 124 is forced out the at least one exhaust port 138. The movement from first state to the second state may be modulated to cause a pulsed flow. As with other embodiments, active control may be incorporated as discussed in connection with FIG. 4. This illustrative embodiment is shown with separate pumps for the two flow circuits, but it should be understood that the same result may be achieved with a single pump and valve arrangement similar to that shown in FIG. 7 to activate the bellows.

While all the embodiments herein are presented in the context of treating a wound, it should be understood that the evaporative subsystem 108 may be used with other applications. For example, the evaporative subsystems may be applied to an inline pouch to process liquids therein.

The wound treatment systems 100 herein include evaporative subsystems 108 that offer a number of perceived advantages and benefits. The systems 100 evaporate and remove liquid from the systems 100, thereby increasing the volume that may be processed by the system 100 or the duration over which the system may operate. In some embodiments, exhaust from the pump is used that otherwise would be wasted. The expensive parts are remote from the dressing and may more easily be accessed. Moreover, the absence of expensive components on the dressing makes disposal easier. These are only some of the possible benefits.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A wound treatment system for treating a wound on a patient, the wound treatment system comprising:
    a treatment manifold for disposing proximate to the wound, wherein the treatment manifold has a first side and a second, patient-facing side;
    a first sealing member for disposing over the first side of the treatment manifold and a portion of intact skin to create a sealed space containing the treatment manifold, wherein the first sealing member comprises a high-moisture-vapor-transfer-rate drape;
    an air-movement manifold having a first side and a second, patient-facing side, wherein the second, patient-facing side is disposed proximate to the first side of the first sealing member;
    a second sealing member disposed over the first side of the air-movement manifold forming a channel space;
    at least one port formed on the second sealing member for allowing air to exit the channel space;
    a reduced-pressure source for producing reduced pressure, wherein the reduced-pressure source is fluidly coupled to the sealed space for delivering reduced pressure thereto;
    a pressure source;
    a Coanda device coupled to the second sealing member and fluidly coupled to the pressure source and to the channel space, wherein the Coanda device comprises:
        an annular nozzle forming a central opening and having an interior passage and a nozzle opening, and a Coanda surface proximate to and downstream from the nozzle opening, whereby fluid exiting the nozzle opening entrains additional fluid from the central opening and produces a combined fluid flow; and wherein the Coanda device is fluidly coupled to a Coanda opening in the second sealing member.

2. The wound treatment system of claim 1, further comprising a bacterial filter coupled to the at least one port.

3. The wound treatment system of claim 1, wherein the Coanda device is configured to pull fluid from the Coanda opening thereby pulling fluid from the at least one port through the air-movement manifold and out the Coanda opening.

4. The wound treatment system of claim 1, wherein the Coanda device is configured to push fluid into the Coanda opening thereby pushing fluid from the Coanda opening through the air-movement manifold and out the at least one port.

5. A wound treatment dressing for treating a wound on a patient, the wound treatment dressing comprising:

a treatment manifold for disposing on the wound, wherein the treatment manifold has a first side and a second, patient-facing side;

a first sealing member for disposing over the first side of the treatment manifold and a portion of intact skin to create a sealed space containing the treatment manifold, wherein the first sealing member comprises a high-moisture-vapor-transfer-rate drape;

an air-movement manifold having a first side and a second, patient-facing side, wherein the second, patient-facing side is disposed proximate to the first side of the first sealing member;

a second sealing member disposed over the first side of the air-movement manifold to form a channel space;

at least one port formed on the second sealing member to allow air to exit the channel space;

a Coanda device coupled to the second sealing member, wherein the Coanda device comprises:

an annular nozzle forming a central opening and having an interior passage and a nozzle opening, and a Coanda surface position proximate to and downstream from the nozzle opening, whereby fluid exiting the nozzle opening entrains additional fluid from the central opening and produces a combined fluid flow; and wherein the Coanda device is fluidly coupled to a Coanda opening in the second sealing member.

6. The wound treatment dressing of claim 5, further comprising a bacterial filter coupled to the at least one port.

7. The wound treatment dressing of claim 5, wherein the Coanda device is configured to pull fluid from the Coanda opening during operation thereby pulling fluid from the at least one port through the air-movement manifold and out the Coanda opening.

8. The wound treatment dressing of claim 5, wherein the Coanda device is configured to push fluid into the Coanda opening during operation thereby pushing fluid from the Coanda opening through the air-movement manifold and out the at least one port.

9. A method for treating a wound on a patient, the method comprising:

disposing a treatment manifold proximate to the wound, wherein the treatment manifold has a first side and a second, patient-facing side;

covering the treatment manifold an a portion of intact skin with a first sealing member to create a sealed space containing the treatment manifold, wherein the first sealing member comprises a high-moisture-vapor-transfer-rate drape and has at least one port;

disposing an air-movement manifold proximate to the first sealing member;

disposing a second sealing member over the air-movement manifold to form a channel space;

fluidly coupling a reduced-pressure source to the sealed space for delivering reduced pressure thereto;

coupling a Coanda device to the second sealing member;

fluidly coupling the Coanda device to a pressure source and to the channel space;

wherein the Coanda device comprises:

an annular nozzle forming a central opening and having an interior passage and a nozzle opening, and a Coanda surface proximate to and downstream from the nozzle opening, whereby fluid exiting the nozzle opening entrains additional fluid from the central opening and produces a combined fluid flow; and fluidly coupling the Coanda device to a Coanda opening in the second sealing member; and providing positive pressure to the Coanda device to cause fluid flow within the air-movement manifold.

10. The method for treating a wound of claim 9, wherein the step of providing positive pressure to the Coanda device comprises intermittently providing positive pressure to the Coanda device.

11. The method for treating a wound of claim 9, wherein the step of providing positive pressure to the Coanda device comprises providing positive pressure to the Coanda device when a saturation sensor indicates that the treatment manifold is saturated.

12. The method for treating a wound of claim 9, wherein the Coanda device is configured to pull fluid from the Coanda opening thereby pulling fluid from the at least one port through the air-movement manifold and out the Coanda opening.

13. The method for treating a wound of claim 9, wherein the Coanda device is configured to push fluid into the Coanda opening thereby pushing fluid from the Coanda opening through the air-movement manifold and out the at least one port.

14. The method for treating a wound of claim 12, wherein a volume $V_1$ of air is delivered to the Coanda device over a time T and wherein a volume $V_2$ of air is delivered through the central opening of the Coanda device over time T whereby an enhanced volume of air is developed ($V_2+V_1$).

15. The method for treating of claim 13, wherein a volume $V_1$ of air is delivered to the Coanda device over a time T and wherein a volume $V_2$ of air is delivered through the central opening of the Coanda device over time T whereby an enhanced volume of air is developed ($V_2+V_1$).

16. The method of claim 9, wherein the step of providing a positive pressure comprises providing a high pressure to the Coanda device and wherein a low pressure flow is created through the central opening.

* * * * *

UNITED STATES PATENT AND TRADEMARK OFFICE
CERTIFICATE OF CORRECTION

| | | |
|---|---|---|
| PATENT NO. | : 9,028,459 B2 | Page 1 of 1 |
| APPLICATION NO. | : 13/442076 | |
| DATED | : May 12, 2015 | |
| INVENTOR(S) | : Richard D. Coulthard et al. | |

It is certified that error appears in the above-identified patent and that said Letters Patent is hereby corrected as shown below:

ON THE TITLE PAGE

Add U.S. Patent Application No. 13/084,813, filed on April 12, 2011 to Related U.S. Application Data section of Title Page.

Signed and Sealed this
Third Day of November, 2015

Michelle K. Lee
*Director of the United States Patent and Trademark Office*